(12) United States Patent
Jalde

(10) Patent No.: US 10,799,658 B2
(45) Date of Patent: Oct. 13, 2020

(54) CONTROL OF MECHANICAL VENTILATION BASED ON LARYNGOPHARYNGEAL MUSCLE ACTIVITY

(71) Applicant: MAQUET CRITICAL CARE AB, Solna (SE)

(72) Inventor: Fredrik Jalde, Sundbyberg (SE)

(73) Assignee: Maquet Critical Care AB, Solna (SE)

( * ) Notice: Subject to any disclaimer, the term of this patent is extended or adjusted under 35 U.S.C. 154(b) by 243 days.

(21) Appl. No.: 15/558,736

(22) PCT Filed: Mar. 26, 2015

(86) PCT No.: PCT/SE2015/050369
§ 371 (c)(1),
(2) Date: Sep. 15, 2017

(87) PCT Pub. No.: WO2016/153406
PCT Pub. Date: Sep. 29, 2016

(65) Prior Publication Data
US 2018/0078721 A1    Mar. 22, 2018

(51) Int. Cl.
*A61M 16/00* (2006.01)
*A61B 5/0488* (2006.01)
(Continued)

(52) U.S. Cl.
CPC ....... *A61M 16/024* (2017.08); *A61B 5/04886* (2013.01); *A61B 5/0803* (2013.01);
(Continued)

(58) Field of Classification Search
CPC .............. A61M 16/00; A61M 16/0003; A61M 16/0051; A61M 16/0057; A61M 16/022;
(Continued)

(56) References Cited

U.S. PATENT DOCUMENTS 5,820,560 A * 10/1998 Sinderby ............ A61B 5/04884
600/546
6,168,568 B1 * 1/2001 Gavriely ................ A61B 5/087
600/529
(Continued)

FOREIGN PATENT DOCUMENTS

CN        1960671 A     5/2007
CN      101057779 A    10/2007
(Continued)

OTHER PUBLICATIONS

Oppersma et al., "Noninvasive Ventilation and the Upper Airway: Should we Pay More Attention/" Critical Care, vol. 17 (2013).
(Continued)

*Primary Examiner* — Joseph D. Boecker
(74) *Attorney, Agent, or Firm* — Schiff Hardin LLP

(57) ABSTRACT

In a method and system for use with a ventilator for mechanical ventilation of a patient, a sensor arrangement registers at least one signal related to muscular activity of at least one muscle in the laryngopharyngeal region of the patient. This signal is provide to a computer, which controls the operation of the ventilator based thereon, and/or causes display of information related to the signal in order monitor the patient and/or operation of the ventilator.

19 Claims, 8 Drawing Sheets

(51) Int. Cl.
*A61B 5/00* (2006.01)
*A61B 5/08* (2006.01)
*A61B 5/087* (2006.01)

(52) U.S. Cl.
CPC ............ *A61B 5/087* (2013.01); *A61B 5/6852* (2013.01); *A61M 16/0003* (2014.02); *A61M 16/0051* (2013.01); *A61B 5/4233* (2013.01); *A61B 5/687* (2013.01); *A61B 5/7282* (2013.01); *A61M 2016/0018* (2013.01); *A61M 2205/17* (2013.01); *A61M 2205/3303* (2013.01); *A61M 2205/502* (2013.01); *A61M 2230/60* (2013.01)

(58) Field of Classification Search
CPC ............ A61M 16/024; A61M 16/04; A61M 2016/0018; A61M 2205/17; A61M 2205/50; A61M 2205/502; A61M 2230/08; A61M 2230/40; A61M 2230/60; A61B 5/04886; A61B 5/0492; A61B 5/0803; A61B 5/087; A61B 5/4233; A61B 5/6852; A61B 5/687; A61B 5/7282; A61N 1/0517
See application file for complete search history.

(56) References Cited

U.S. PATENT DOCUMENTS

| | | | | |
|---|---|---|---|---|
| 6,588,423 | B1* | 7/2003 | Sinderby | A61B 5/04884 128/200.24 |
| 2005/0211246 | A1 | 9/2005 | Beck et al. | |
| 2006/0037615 | A1* | 2/2006 | Wilkinson | A61B 5/08 128/204.23 |
| 2008/0121231 | A1 | 5/2008 | Sinderby et al. | |
| 2008/0167675 | A1* | 7/2008 | Hogosta | A61B 5/037 606/196 |
| 2009/0151719 | A1 | 6/2009 | Wondka et al. | |
| 2009/0241946 | A1 | 10/2009 | Simlowski et al. | |
| 2011/0226248 | A1 | 9/2011 | Duff et al. | |
| 2012/0215126 | A1* | 8/2012 | Gavriely | A61B 5/097 600/538 |
| 2014/0296728 | A1* | 10/2014 | Sinderby | A61B 5/08 600/529 |
| 2014/0305434 | A1* | 10/2014 | Beck | A61M 16/04 128/203.14 |
| 2016/0310069 | A1* | 10/2016 | Sinderby | A61B 5/0452 |

FOREIGN PATENT DOCUMENTS

| | | |
|---|---|---|
| DE | 102004011078 A1 | 9/2005 |
| GB | 2 294 642 A | 5/1996 |
| WO | WO-99/43374 A1 | 9/1999 |
| WO | 2008/131798 A1 | 11/2008 |

OTHER PUBLICATIONS

China National Intellectual Property Administration, Office Action issued for CN 201580078122.5, 8 pgs., dated Oct. 10, 2019.

European Search Report dated Jun. 24, 2020 for European Patent No. 20165215.3.

* cited by examiner

CONTROL OF MECHANICAL VENTILATION BASED ON LARYNGOPHARYNGEAL MUSCLE ACTIVITY

BACKGROUND OF THE INVENTION

Field of the Invention

The present invention relates to the field of mechanical ventilation. In particular, the present invention relates to detection of signals relating to muscular activity of breathing-related muscles of a subject, and use of such signals in the control of a mechanical ventilator providing support ventilation to said subject.

Description of the Prior Art

In the field of mechanical ventilation, there are various techniques for adjusting the ventilation pattern provided by the ventilator to the patient's own breathing efforts. Ventilation modes in which the ventilator adapts the supply of breathing gas to detectable breathing efforts of a ventilated patient are generally referred to as modes of assisted or supported ventilation. More commonly, a ventilator that is operated in such a ventilation mode is said to provide support ventilation to the patient.

In recent years there has evolved techniques for neurally adjusted ventilation, i.e. techniques in which the ventilation pattern provided to the patient by the ventilator is adapted to the breathing efforts of the patient by controlling the supply of breathing gas by the ventilator based on neurological signals indicating at least the points in time at which there is a desire of the patient to inhale and/or exhale. An example of such a technique is the now clinically well-established technique of Neurally Adjusted Ventilatory Assist (NAVA).

The act of taking a breath is controlled by the respiratory center of the brain, which decides the characteristics of each breath, timing and size. The respiratory center sends a signal along the phrenic nerve, excites the diaphragm muscle cells, leading to muscle contraction and descent of the diaphragm dome. As a result, the pressure in the airway drops, causing an inflow of air into the lungs.

With NAVA, the electrical activity of the diaphragm (Edi) is captured, fed to a NAVA-enabled ventilator and used to assist the patient's breathing in synchrony with and in proportion to the patient's own breathing efforts. As the work of the ventilator and the diaphragm is controlled by the same signal, coupling between the diaphragm and the NAVA-enabled ventilator is synchronized simultaneously.

The NAVA technology is further described in e.g. WO 1998/48877, WO 1999/62580, WO 2006/131149, and WO 2008/131798.

The Edi is typically captured by measuring the electromyogram (EMG) of the contracting diaphragm, sometimes referred to as diaphragm EMG. The EMG signals are then processed in various ways and a signal representative of the Edi is calculated and used in the control of the NAVA-enabled ventilator, typically by controlling the supply of breathing gas to the patient in synchrony and in proportion to the Edi.

Typically, the EMG signals representative of said Edi signal are measured by means of an array of electrodes arranged along an esophageal catheter inserted into the esophagus of the patient. Such a catheter is often referred to as a NAVA catheter and is described in more detail in for example U.S. Pat. Nos. 5,671,752 and 7,021,310.

Instead or in addition to a NAVA catheter for picking up signals from within the patient, a set of chest wall surface electrodes may be used to record the diaphragm EMG from the surface of the skin of the patient. Just like the EMG signals picked up by the NAVA catheter, the diaphragm EMG recorded by means of such surface electrodes may be used to derive a diaphragm Edi signal of the patient, which Edi signal may be used in the control of a NAVA-enabled ventilator operated in NAVA mode.

In some situations, the EMG signals registered by the NAVA catheter or the chest wall surface electrodes are weak or not truly representative of the Edi of the patient, thereby rendering NAVA ventilation unsuitable. One challenge within the field of NAVA ventilation is detection and verification of such situations. Another challenge is how to best handle the situation in which absence of a reliable Edi signal can be verified.

Yet another challenge within the field of NAVA ventilation is how to make control of the ventilator more robust in situations in which the Edi signal alone does not provide sufficient or sufficiently reliable information on the physiological state or the desired respiratory pattern of the ventilated patient.

SUMMARY OF THE INVENTION

It is an object of the present invention to provide an improved or at least alternative way of controlling a ventilator providing support ventilation to a patient. In particular, it is an object of the invention to provide an improved or at least alternative way of providing neurally adjusted ventilatory assist (NAVA) to a patient, meeting one or more of the above-mentioned challenges of conventional NAVA ventilation.

Another object of the invention is to provide an improved or at least alternative bioelectric sensor arrangement for use during mechanical ventilation of a patient.

According to one aspect of the present invention there is provided a system for use in connection with mechanical ventilation of a patient, provided by a ventilator. The system comprises a sensor arrangement configured to register at least one signal related to muscular activity of at least one muscle in the laryngopharyngeal region of the patient. Further, the system comprises at least one control unit configured to control the operation of said ventilator based on said at least one registered signal, and/or to cause display of information related to said at least one registered signal on at least one display unit.

The at least one display unit may be a display unit of the ventilator and/or a display unit of a stand-alone monitoring system for monitoring the status of the patient and/or the operation of the ventilator. The display of information related to the registered signal may serve as a decision support to an operator who manually or partially manually controls the operation of the ventilator based on e.g. information displayed on said display unit, including but not limited to said registered signals.

Thus, the present invention presents a system allowing the operation of a ventilator to be automatically or manually controlled based on information contained in a signal related to the muscular activity of at least one muscle in the laryngopharyngeal region of the patient. Such a signal will hereinafter be referred to as a laryngopharyngeal signal (LP signal). The muscular activity of some muscles in this region is controlled by the respiratory center of the brain and so indicative of the patient's efforts to breathe. Thus, the at least one LP signal registered by the sensor arrangement and related to said muscular activity provides information which alone or in combination with other information indicative of the patient's breathing efforts can be used to adapt the operation of the ventilator to the needs of the patient, e.g. to make the ventilator supply breathing gas to the patient in synchrony with and in proportion to the patient's own breathing efforts.

The LP signal can be used in any type of support ventilation mode to better adapt the ventilation provided by the ventilator to the patient's own breathing efforts. For example, the LP signal may be used as control signal during pressure support ventilation or NAVA ventilation of a patient, instead or in addition to the control parameters normally used in those modes of support ventilation.

To some extent the invention can also be said to provide a novel type of mechanical ventilation support mode, which novel type of support mode has much in common with the conventional NAVA mode since this novel type of support mode also provides neurally adjusted ventilatory assist to the patient. However, while in conventional NAVA controlling the ventilator based on the diaphragm EMG ($EMG_{Dia}$), i.e. EMG signals related to the muscular activity of the diaphragm, the present invention provides the possibility of operating the ventilator in a support mode in which it is controlled based on LP signals related to the muscular activity of muscles in the laryngopharyngeal region. Conventional NAVA in which ventilation is controlled based on $EMG_{Dia}$ will hereinafter be referred to as diaphragmatic NAVA ($NAVA_{Dia}$), whereas the novel type of neurally adjusted ventilatory assist that is controlled based on LP signals will be referred to as laryngopharyngeal NAVA ($NAVA_{LP}$).

In some embodiments of the present disclosure, both LP signals and $EMG_{Dia}$ are used to control the ventilator. This ventilation mode will be referred to as diaphragmatic/laryngopharyngeal NAVA ($NAVA_{Dia/LP}$).

The sensor arrangement of the invention is hence configured to register at least one LP signal that is related to the muscular activity of at least one muscle of the laryngopharyngeal region. Preferably, the sensor arrangement is configured to register at least one LP signal that is related to the muscular activity of at least one muscle in the laryngeal region, i.e. at least one laryngeal muscle. Even more preferably, the sensor arrangement is configured to register at least one LP signal indicative of the muscular activity of the thyroarytenoid muscle (hereinafter referred to as the TA muscle) and/or the cricothyroid muscle (hereinafter referred to as the CT muscle). Most preferably, the registered LP signal is indicative of the activity of the TA muscle.

Thus, the sensor arrangement may be configured to register at least one signal, herein referred to as an LP signal, which at least one signal is related to muscular activity of the TA muscle and/or the CT muscle caused by a breathing-related bioelectric signal transmitted to said muscle(s) from the respiratory center of the patient's brain, and so indicative of the patient's desire to breathe.

In some embodiments, the sensor arrangement for registering the at least one LP signal may be an optical sensor arrangement, such as a fiberoptic bronchoscope, configured to register the LP signal based on the patency of the glottic opening.

In other embodiments, the sensor arrangement for registering the at least one LP signal may be a bioelectric sensor arrangement configured to register LP signals in form of bioelectric signals originating from muscles in the laryngopharyngeal region. For example, the sensor arrangement may be a bioelectric sensor arrangement configured to register the laryngopharyngeal EMG ($EMG_{LP}$), i.e. EMG signals related to the muscular activity of muscles in the laryngopharyngeal region.

In some embodiments, said bioelectric sensor arrangement may be configured to register the LP signal non-invasively from outside the patient. For example, it is contemplated that the sensor arrangement may comprise a set of surface electrodes configured to be attached to the skin of the patient's neck, in particular to the area around the throat of the patient, in order to register the $EMG_{LP}$ of the patient from the surface of the skin. Preferably, said set of surface electrodes comprises at least two surface electrodes for registering LP signals. Additionally, the set of surface electrodes may comprise a reference electrode for capturing a reference signal which may be used for noise suppression by a signal processing unit supplied with the signals captured by the electrodes.

In other embodiments, however, said bioelectric sensor arrangement is configured to register the LP signal from within the patient. In a preferred embodiment, the bioelectric sensor arrangement comprises an esophageal catheter configured to be inserted into the esophagus of a patient who is to be mechanically ventilated by a ventilator. The esophageal catheter may comprise at least one electrode, hereinafter referred to as an LP electrode, configured to register $EMG_{LP}$ signals related to the muscular activity of muscles in the laryngopharyngeal region when the catheter is inserted into the esophagus of the patient. Thereby, the present disclosure presents a novel type of bioelectric sensor which is similar to a conventional NAVA catheter but differs therefrom at least in the location of the electrodes for picking up the bioelectric signals and/or the length of the catheter. This novel type of esophageal catheter may hereinafter be referred to as a $NAVA_{LP}$ catheter to distinguish it from a conventional NAVA catheter for picking up $EMG_{Dia}$, signals, which conventional catheter is hereinafter referred to as a $NAVA_{Dia}$ catheter.

In some embodiments, the esophageal catheter may further comprise at least one electrode, hereinafter referred to as a diaphragm electrode, configured to register $EMG_{Dia}$ signals related to the muscular activity of the diaphragm of the patient when the catheter is inserted into the esophagus. This makes the esophageal catheter a combined $NAVA_{LP}$ and $NAVA_{Dia}$ catheter, hereinafter referred to as a N-$AVA_{Dia/LP}$ catheter, comprising both at least one LP electrode for registering $EMG_{LP}$ in the laryngopharyngeal region of the patient and at least one diaphragm electrode for registering $EMG_{Dia}$ in the diaphragmatic region of the patient.

Furthermore, the $NAVA_{Dia/LP}$ catheter may comprise at least one reference electrode which may be located between the at least one LP electrode and the at least one diaphragm electrode, i.e. in between said LP zone and said diaphragm zone. In one embodiment, the $NAVA_{Dia/LP}$ catheter comprises an upper array of at least two LP electrodes, a lower array of at least two diaphragm electrodes, and at least one reference electrode located between said upper array of LP electrodes and said lower array of diaphragm electrodes. In another embodiment, the $NAVA_{Dia/LP}$ catheter comprises an upper array of five LP electrodes, a lower array of four diaphragm electrodes, and one reference electrode located between said upper and lower electrode arrays. The use of two or more electrodes of each type is advantageous in that any two adjacent electrodes then form an electrode pair for registering signals from which a differential signal representative of the $EMG_{LP}$ or $EMG_{Dia}$ signal can be derived.

Furthermore, the system typically comprises a signal processing unit configured to receive the LP signals from the sensor arrangement and to derive, from said signals, one or more processed signals which may be used in automatic control of the ventilator and/or displayed on said display unit in order to serve as decision support for an operator in manual or partially manual control of the ventilator.

In embodiments wherein the sensor arrangement comprises a $NAVA_{LP}$ catheter or a $NAVA_{Dia/LP}$ catheter, said signal processing unit may be configured to receive the $EMG_{LP}$ signals from the LP electrodes of the catheter, and to derive from said $EMG_{LP}$ signals a signal representative of the electric activity of the muscles of the laryngopharyngeal region. This signal will hereinafter be referred to as the Elp signal and can be said to correspond to the Edi signal of conventional NAVA ($NAVA_{Dia}$), which Edi signal is derived from the $EMG_{Dia}$ signals and used as control signal during conventional $NAVA_{Dia}$ ventilation. In more detail, the signal processing unit is typically configured to receive raw signals from said LP electrodes, which raw signals comprise $EMG_{LP}$ components and noise, extract the $EMG_{LP}$ signals from said received raw signals, and derive the Elp signal from said extracted $EMG_{LP}$ signals.

It should thus be appreciated that in one embodiment of the present disclosure, the signal processing unit may be configured to derive an Elp signal from LP signals comprising $EMG_{LP}$ signals, registered by means of a bioelectric sensor, e.g. a $NAVA_{LP}$ or $NAVA_{Dia/LP}$ catheter, and to transmit the Elp signal to a control unit for controlling a ventilator based on said Elp signal and/or for causing display of the Elp signal on a display unit. The module of the signal processing unit that is configured to derive the Elp signal from the LP signals received from the sensor arrangement will hereinafter be referred to as the $EMG_{LP}$ module.

The $EMG_{LP}$ module may in some embodiments form part of a signal processing unit especially adapted for use with a $NAVA_{Dia/LP}$ catheter. In this case, said processing unit may further comprise an $EMG_{Dia}$ module configured to receive $EMG_{Dia}$ signals captured by means of the diaphragm electrodes of the $NAVA_{Dia/LP}$ catheter, derive an Edi signal from said $EMG_{Dia}$ signals, and to transmit the Edi signal to the control unit for controlling the ventilator based on both the Edi signal and said Elp signal, and/or for causing display of both the Edi signal and said Elp signal on said display unit, and/or information derived from both the Edi signal and the Elp signal. In more detail, said $EMG_{Dia}$ module, corresponding to the what is often referred to as the Edi module in the field of conventional NAVA, is configured to receive raw signals from said diaphragm electrodes, which raw signals comprise $EMG_{Dia}$ components, noise and typically also ECG components originating from the electrical activity of the patients heart, extract the $EMG_{Dia}$ signals from said received raw signals, and derive the Edi signal from said extracted $EMG_{Dia}$ signals.

The signal processing unit may further comprise another module, hereinafter referred to as the comparator, configured to compare the Elp signal with the Edi signal. The at least one control unit of the system may be configured to control the operation of the ventilation and/or to cause display of information on said at least one display unit based on the result of said comparison.

In embodiments in which the operation of the ventilator is controlled based on the Edi signal, said comparator may be configured to compare the Edi signal with the Elp signal to validate the reliability of the Edi signal, and to cause the ventilator to switch from the current Edi-controlled mode of operation to a ventilation mode not dependent on said Edi signal in case the reliability of the Edi signal cannot be validated.

Thus, according to one aspect of the present disclosure, there is provided a system providing for an enhanced mode of NAVA ventilation in which at least one LP signal related to muscular activity of at least one muscle in the laryngopharyngeal region of the patient is used to validate the accuracy of the Edi signal controlling the operation of the NAVA ventilator, and to prevent that the ventilator is controlled based on inaccurate readings of said Edi signal. This functionality is offered in the enhanced mode of NAVA ventilation, $NAVA_{Dia/LP}$, made available by the system of the present disclosure.

Controlling mechanical ventilation of a patient based on registered LP signals in accordance with the principles of the present disclosure may be advantageous during both invasive and non-invasive ventilation (NIV). However, it is particularly advantageous during NIV since the activity of the laryngopharyngeal muscles does not affect invasive ventilation to the same extent as NIV. During NIV, wherein the patient interface is constituted by e.g. a face mask or a nasal prong, the breathing gas supplied by the ventilator passes the upper respiratory tract of the patient, including the laryngopharyngeal region, and so the muscular activity of the muscles therein greatly affects the result of the NIV. During invasive ventilation, however, wherein the patient interface is constituted by e.g. a tracheal tube, the breathing gas supplied by the ventilator bypasses the laryngopharyngeal region of the patient which makes invasive ventilation insensitive or at least less sensitive to the muscular activity in this area.

The difficulties of NIV and the impact on NIV of the muscle activity of the muscles in the upper respiratory tract, including the laryngopharyngeal region, are discussed in the article "Noninvasive ventilation and the upper airway: should we pay more attention?," Oppersma et al, Critical Care 2013, 17:245, and further in the article "Absence of inspiratory laryngeal constrictor muscle activity during nasal neurally adjusted ventilatory assist in newborn lambs", Hajd-Ahmed et al., Journal of Applied Physiology, 113:63-70, 2012.

Since the LP signals registered by the sensor arrangement of the present invention carries information on the muscular activity in the laryngopharyngeal region, the present invention provides for improved NIV ventilation since this information can be used automatically or manually to adapt the NIV ventilation to compensate for said muscular activity.

Consequently, according to one embodiment of the present disclosure, there is provided a system for use in connection with mechanical non-invasive ventilation of a patient, provided by a ventilator connected to a patient by means of a non-invasive patient connector, such as a face mask or a nasal prong. The system comprises at least a sensor arrangement and a control unit devised and configured as set forth above. The at least one control unit may further be configured to automatically adjust the operation of the ventilator based on the at least one registered LP signal to compensate for the influence of muscular activity in the laryngopharyngeal region on the NIV ventilation, as indicated by said at least one LP signal.

As previously discussed, the LP signals registered by the sensor arrangement of the invention may be used to control the operation of the ventilator in different ways in different modes of support ventilation.

In one embodiment, the at least one control unit of the system is configured to use the at least one registered LP signal in the determination of when to switch from one respiratory phase of the ventilator to another, i.e. from ventilator inspiration to ventilator expiration or vice versa.

In particular, the control unit may be configured to use the at least one LP signal in the determination of when to initiate the inspiratory/expiratory (IE) phase transition, sometimes referred to as the inspiratory off-switch (IOS) or the inspiratory cycle-off (ICO), i.e. to determine the point in time at which the ventilator should switch from inspiration to expiration. The laryngopharyngeal muscle activity is generally low (the upper airway is open) during desired inspiration of the patient in order for breathing gas to flow freely through the upper airway and onto the lungs of the patient. The low level of muscle activity in the laryngopharyngeal region results in a weak LP signal during desired inspiration of the patient. When the patient wishes to stop inspiration and start expiration, the muscle activity in the laryngopharyngeal region increases (the upper airways are temporarily closed), resulting in a sudden increase in the registered LP signal. The control unit may be configured to use this increase in LP signal amplitude to determine the point in time at which the ventilator should initiate the ICO, e.g. by determining when the LP signal exceeds a predetermined threshold value serving as an LP signal trigger level for initiation of ICO.

Using the LP signal to determine when to initiate ICO may be advantageous in any supported mode of ventilation, including but not limited to conventional NAVA ($NAVA_{Dia}$), pressure support (PSV), and volume support (VSV). The control unit may be configured to determine when to initiate ICO based on the at least one LP signal alone or based on a combination of the at least one LP signal and one or more other indicators of the patient's desire to initiate ICO.

For example, in NAVA modes or neurally triggered pneumatic modes in which the Edi signal is available, the control unit may be configured to determine when to initiate ICO based on a comparison between the LP signal and the Edi signal. This may provide for more robust control of ICO. Contrary to the LP signal, the Edi signal becomes weaker when the patient wishes to stop inspiration and start expiration. In one embodiment the control unit may be configured to determine when the amplitude of the Edi signal falls below a predetermined threshold value serving as an Edi signal trigger level for initiation of ICO. The control unit may for example be configured to initiate ICO when, and only when, the LP signal and the Edi signal have reached their respective trigger levels for initiation of ICO. The control unit may thus be configured to prevent initiation of ICO based on said Edi signal as long as the amplitude of the LP signal falls below a predetermined value, thereby preventing false trigging of ICO.

Instead or in addition to the Edi signal, measured pressure and/or flow values indicative of the patient's desire to stop inspiration and start expiration can be used in combination with the LP signal for more robust control of ICO. For example, as well known in the art, flow and/or pressure in the inspiratory line of the ventilator or patient circuit connecting the ventilator and the patient may be used as an indicator of the patient's desire to switch from inspiration to expiration. The control unit may be configured to use a signal indicative of said flow and/or pressure together with the LP signal in the determination of when to initiate ICO. In particular in the pressure support mode of ventilation (PSV), the lack of a robust criterion for initiation of ICO is a well-recognized problem. Monitoring and using an LP signal relating to the laryngopharyngeal muscle activity in the determination of when to initiate ICO may hence serve to solve or at least mitigate this problem.

Furthermore, the at least one control unit of the system may be configured to use the at least one registered LP signal to automatically adjust the level of ventilatory assist provided to the patient by the ventilator, and/or to signal that the level of ventilatory assist should be adjusted to an operator of the ventilator. A strong LP signal during ventilator inspiration typically indicates that the muscles of the laryngopharyngeal region strive to decrease the flow of breathing gas flowing into the lungs of the patient, and so that the level of ventilatory assist (i.e. the flow and/or pressure of breathing gas provided to the patient) is currently too high. The control unit may be configured to determine whether the level of ventilatory assist should be adjusted based on the inspiratory LP signal, i.e. the LP signal registered during ventilator inspiration. For example, the control unit may be configured to compare the inspiratory LP signal with a threshold value and, if the threshold value is exceeded, to automatically adjust the level of ventilatory assist and/or to signal that the level of ventilatory assist should be adjusted to an operator of the ventilator, e.g. by generating a visual and/or audible alarm.

However, that the LP signal is strong during ventilator inspiration does not necessarily imply that the assist level is too high. That the LP signal is strong may also be due to a mismatch or asynchrony between the respiratory phases of the ventilator and the respiratory phases of the patient. Therefore, the control unit is preferably configured to determine, based on the LP signal, whether there is synchrony or asynchrony between the respiratory phases of the ventilator and the respiratory phases of the patient, and to automatically adjust the level of ventilatory assist and/or to signal that the level of ventilatory assist should be adjusted only in case of synchrony between said phases. In ventilation modes in which the timing of transitions between inspiration and expiration phases are controlled based on an Edi signal captured from the patient, synchrony/asynchrony between the respiratory phases of the ventilator and respiratory phases of the patient can be determined by the control unit by determining, the synchrony/asynchrony between the Edi signal and the LP signal. Thus, to distinguish the situation of too high assist level (in which case the assist level should be decreased) from the situation of asynchrony between the respiratory phases of the ventilator and the patient, the control unit may be configured to compare the LP signal and the Edi signal. Consequently, in embodiments where the Edi signal of the patient is available, the control unit may be configured to determine whether the ventilatory assist level should be adjusted based on a comparison between the Edi signal and the LP signal.

If it is determined that the level of ventilatory assist needs to be adjusted, the control unit may be configured to automatically determine an appropriate level of ventilatory assist by causing the ventilator to switch between different levels of ventilatory assist, e.g. every fifth breath, and to determine the appropriate level of ventilatory assist based on a change in the registered LP signal between the different levels of ventilatory assist. For example, the control unit may be configured to determine the appropriate level of ventilatory assist through a titration process during which the control unit causes a stepwise decrease in ventilatory assist level and determines the appropriate level of ventilatory assist as the upper level of two levels between which the change in amplitude of the registered LP signal is less than a predetermined threshold value, and preferably nearly zero. Thus, the control unit may be configured to determine an appropriate level of ventilatory assist based on the LP signal response to at least one change in ventilatory assist level.

Furthermore, the at least one control unit of the system may be configured to use the at least one registered LP signal to automatically adjust a level of positive end-expiratory pressure (PEEP) applied to the patient, and/or to signal that the level of PEEP should be adjusted to an operator of the ventilator. A strong LP signal during ventilator expiration typically indicates that the muscles of the laryngopharyngeal region strive to maintain the pressure within the lungs by quenching the expiration flow of gas out of the upper airway, which in turn may be taken as an indication of a need for increased PEEP. Thus, the control unit may be configured to determine whether the current PEEP level should be adjusted based on the expiratory LP signal, i.e. the LP signal registered during ventilation expiration. For example, the control unit may be configured to compare the expiratory LP signal with a threshold value and, if the threshold value is exceeded, to automatically adjust the PEEP level and/or to signal that the PEEP level should be adjusted to an operator of the ventilator, e.g. by generating a visual and/or audible alarm.

However, that the LP signal is strong during ventilator expiration does not necessarily imply that the PEEP level is too low. In accordance with the above reasoning with regard to the relation between the LP signal and the level of ventilatory assist, the fact that the LP signal is strong may also be due to a mismatch or asynchrony between the respiratory phases of the ventilator and the breathing efforts of patient. Therefore, the control unit is preferably configured to determine whether there is synchrony or asynchrony between the respiratory phases of the ventilator and the respiratory phases of the patient, and to automatically adjust the PEEP level and/or to signal that the PEEP level should be adjusted only in case of synchrony between said phases. The synchrony/asynchrony between the respiratory phases of the ventilator and respiratory phases of the patient may be determined by the control unit based on a comparison between the Edi signal and the LP signal, as described above. Consequently, in one embodiment, the control unit may be configured to determine whether the PEEP level should be adjusted based on a comparison between the Edi signal and the LP signal.

If it is determined that the PEEP level needs to be adjusted, the control unit may be configured to automatically determine an appropriate level of PEEP by causing the ventilator to switch between different PEEP levels, e.g. every fifth breath, and to determine the appropriate level of PEEP based on a change in the registered LP signal between the different PEEP levels. For example, the control unit may be configured to determine the appropriate level of PEEP through a titration process during which the control unit causes a stepwise increase in PEEP level and determines the appropriate level of PEEP as the lower level of two levels between which the change in amplitude of the registered LP signal is less than a predetermined threshold value, and preferably nearly zero. Thus, the control unit may be configured to determine an appropriate PEEP level based on the LP signal response to at least one change in PEEP level.

As discussed above, the at least one control unit of the system may be configured to use the at least one registered LP signal to detect ventilator-patient asynchrony, i.e. asynchrony between the respiratory phases of the ventilator and the desired respiratory phases of the patient as indicated by detectable respiratory efforts. In a similar manner, the control unit may be configured to detect false triggering of respiration phases, and in particular inspiration phases, in patient-triggered ventilation modes. The LP signal may be used to detect both pneumatic false-triggering, i.e. false-triggering based on measured pressure and/or flow, and neural false-triggering, i.e. false-triggering based on a measured neural signal, such as the Edi signal. Thus, the LP signal may be advantageously used by the control unit in detection of false-triggering in both pneumatically controlled support modes, such as pressure support (PSV) and volume support (VSV), and in neurally controlled modes, such as NAVA. False-triggering is a well-recognized problem within the field of mechanical ventilation, in particular during NIV ventilation (due to leakage in the patient interface), and false-triggered breaths are difficult to detect by means of the sensors normally included in ventilation systems according to prior art. The LP signal detected by the sensor arrangement of the present disclosure hence offers a longed-for possibility of detecting false-triggering in a reliable manner.

Furthermore, the control unit of the system may be configured to use the at least one registered LP signal to detect reverse phase respiration, i.e. a situation in which the respiratory phases of the ventilator and the patient are reversed in relation to each other. Reverse phase respiration is a problem mainly during ventilation in NAVA mode.

The control unit is preferably configured to detect false-triggering and/or reverse phase respiration based on the inspiratory LP signal. If the level of ventilatory assist is appropriate, a strong inspiratory LP signal (the LP signal registered during ventilation inspiration) may indicate that ventilator inspiration is initiated during patient expiration, causing activation of the laryngopharyngeal muscles of the patient to obstruct the undesired flow of inspiration gas received from the ventilator. In patient-triggered support modes of ventilation, initiation of ventilator inspiration during patient expiration can only be caused by false-triggering (in pneumatic support modes or NAVA) or reverse phase respiration (in NAVA). Thus, the control unit may be configured to detect false-triggering and/or reverse phase respiration based on the LP signal by comparing the inspiratory LP signal with a threshold value, whereby false-triggering and/or reverse phase respiration is detected in case said threshold value is exceeded. In case of detection of false-triggering and/or reverse phase respiration, the control unit may be configured to automatically adjust the operation of the ventilator to avoid or at least mitigate the risk of false-triggering and/or reverse phase respiration, and/or to generate an alarm notifying the ventilator operator of the detected false-triggering and/or reverse phase respiration, e.g. in form of a visual alarm displayed on a display unit.

That the level of ventilatory assist is appropriate, and thus that the strong inspiratory LP signal is not caused by a too high level of ventilatory assist, may be determined by the control unit in different ways. For example, the control unit may be configured to use the above described titration process for automatic determination or verification of the appropriate level of ventilatory assist. Furthermore, in pressure support mode, a sudden change in the inspiratory LP signal, especially during short breaths, may indicate that the ventilatory assist level is appropriate and that said short breaths are false-triggered. The control unit may be configured to use the level of the inspiratory LP signal during such short and false-triggered breaths to determine or adjust the above-mentioned threshold value with which the inspiratory LP signal may be compared in order to detect false-triggering and/or reverse phase respiration. Yet further, if the Edi signal is monitored in pressure support mode, the control unit may determine whether the level of ventilatory assist provided to the patient is appropriate by comparing the ventilator settings and/or measured pressure and/or flow values with the registered Edi signal. How to verify that the level of ventilatory assist is suitably adjusted to the needs of the patient as manifested by the Edi signal is well known in the art of NAVA. In NAVA, it is assumed that ventilatory assist is provided in synchrony with and proportion to the patient's own breathing, and so it must be assumed that a sudden increase in the inspiratory LP signal is caused by false-triggering or reverse phase respiration.

A problem associated with conventional NAVA ventilation ($NAVA_{Dia}$), however, is false detection of reverse phase respiration. If the esophageal catheter is inserted too far into the esophagus of the patient, the diaphragm electrodes may register bioelectric signals from the abdominal muscles instead of the diaphragm. The abdominal muscles work in reverse phase in relation to the diaphragm, and controlling the ventilator based on bioelectric signals from the abdominal muscles may hence cause reverse phase respiration. NAVA ventilators of today contain algorithms for detecting such a faulty condition, and to switch ventilation mode from NAVA to pressure support (NAVA (PS)) in case of detection of reverse phase respiration. However, said algorithms are not very robust and false detection of reverser phase respiration is rather common. Such false detections cause the ventilator to undesirably switch from NAVA mode to said pressure support mode. The system of the present disclosure offers a solution to this problem since the control unit of the system can be configured to prevent the ventilator from switching from NAVA to pressure support mode unless analysis of the registered LP signal verifies the alleged detection of reverse phase respiration. Thus, the at least one control unit may be configured to determine, during ongoing NAVA ventilation, whether to switch to another ventilation mode not dependent on the Edi signal, such as a pressure support mode, based on the registered LP signal. In particular, the control unit may be configured to verify, based on the registered LP signal, an alleged detection of reverse phase respiration, and to prevent the ventilator from switching from the NAVA mode to another mode of ventilation unless reverse flow ventilation can be verified. Since the LP signal, like the Edi signal, is indicative of the patient's breathing efforts and so the desired respiratory pattern of the patient, the control unit may verify or contest the alleged situation of reverse flow respiration by studying the LP signal during ventilator inspiration and/or expiration (i.e. the inspiratory and/or expiratory LP signal). If the LP signal looks normal, i.e. the way it looks like when ventilator respiration and patient respiration are synchronized and in phase with each other, the alleged detection of the reverser phase respiration can be ignored and the ventilator can remain in the NAVA mode of ventilation.

According to another aspect of the present disclosure, there is provided a computer program which, when executed by the at least one control unit of the system, causes the operation of the ventilator to be based on the at least one registered LP signal, and/or causes display of information related to said at least one LP signal on said display unit for monitoring the patient and/or the operation of the ventilator.

The computer program comprises computer-readable instructions, e.g. in form of program code, which for example may be stored in a non-volatile memory of said at least one control unit. When executed by the control unit, e.g. by means of at least one processor of the control unit, the computer-readable instructions causes the control unit to perform, or to cause other system components to perform, the above described steps related to use of the at least one LP signal registered by the sensor arrangement.

More advantageous aspects and effects of the method as well as the gas delivery system and the additive gas delivery apparatus of the invention will be described in the detailed description following hereinafter.

DESCRIPTION OF THE PREFERRED EMBODIMENTS

Figure 1:
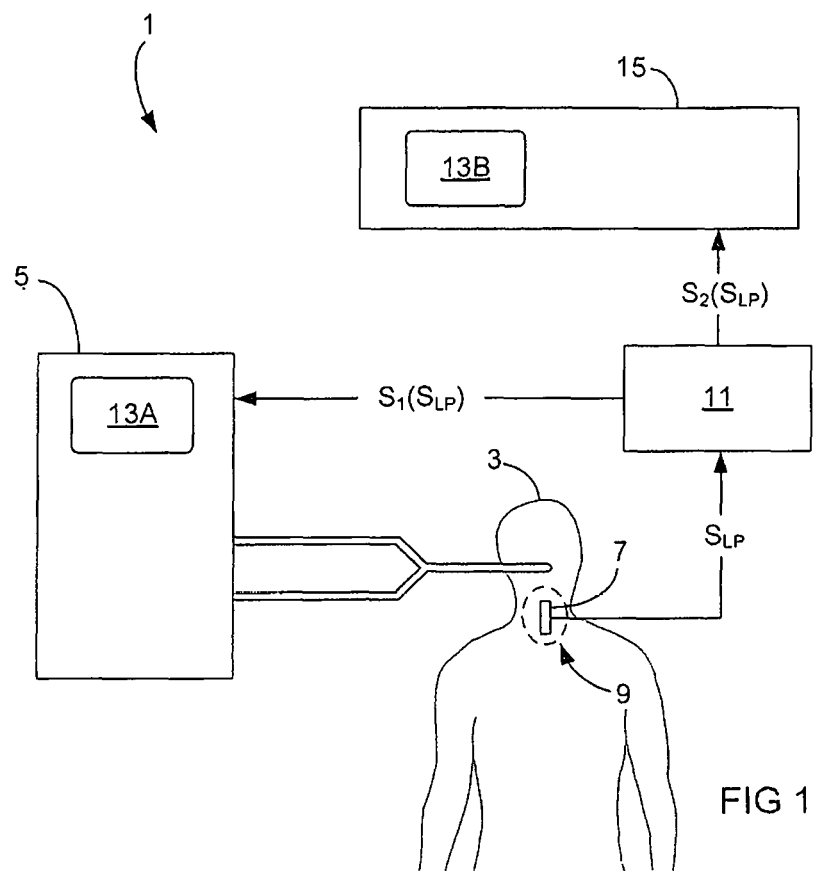
FIG. 1 illustrates a system for use in connection with mechanical ventilation of a patient, according to an exemplary embodiment of the invention.

FIG. 1 illustrates a system 1 for use in connection with mechanical ventilation of a patient 3, provided by a ventilator 5. The system comprises at least a sensor arrangement 7 configured to register at least one signal, $S_{LP}$, related to muscular activity of at least one muscle in the laryngopharyngeal region 9 of the patient 3. Such a signal is herein referred to as a laryngopharyngeal signal (LP signal). Further, the system 1 comprises at least one control unit 11 configured to control the operation of said ventilator based on the at least one registered LP signal, and/or to cause display of information related to said at least one registered LP signal on at least one display unit 13A, 13B.

The at least one display unit 13A, 13B may be a display unit 13A of the ventilator 5 and/or a display unit 13B of a stand-alone monitoring system for monitoring the status of the patient 3 and/or the operation of the ventilator 5.

That the operation of the ventilator 5 is controlled based on the registered LP signal means that the ventilator 5 is controlled based on the signal, SLP, captured by the sensor arrangement 7, or a signal, S1(SLP), derived therefrom, which signal is dependent on the signal, SLP, captured by the sensor arrangement 7. Likewise, that information related to the registered LP signal is displayed on a display unit 13A, 13B means that the at least one captured signal itself, SLP, is displayed on the display unit, or that a signal, S2(SLP), or any other information derived from the captured signal is displayed on said display unit 13A, 13B.

In FIG. 1, the at least one control unit 11 is illustrated as a separate unit. However, it should be appreciated that the at least one control unit 11 of the present invention may be integrated in the ventilator 5 and/or the monitoring system 15. For example, the sensor arrangement 7 may be connected directly to the ventilator 5 in order for an internal control unit of the ventilator 5 to use the registered LP signal as control signal for controlling the operation of the ventilator, and/or for causing display of information related thereto on the display unit 13A of the ventilator 5. The sensor arrangement 7 may also be directly connected to the monitoring system 15 in order for an internal control unit of the monitoring system to cause display of information related to the registered LP signal on the display unit 13B of the monitoring system 15.

Figure 2:
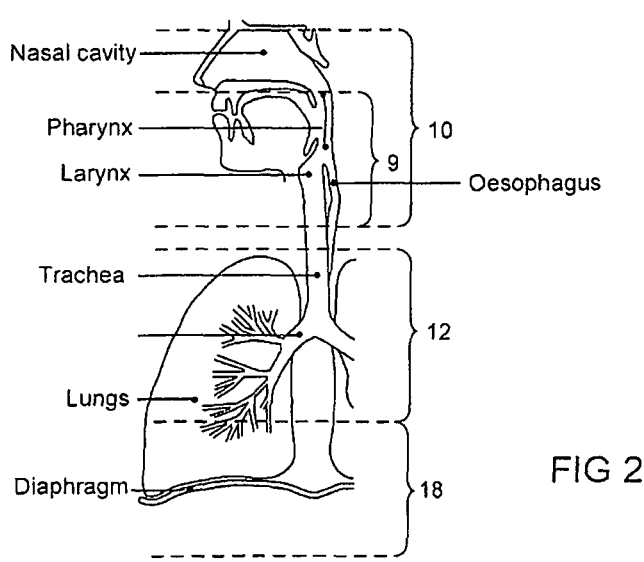
FIG. 2 illustrates the respiratory tract of a human being.

FIG. 2 illustrates the respiratory tract of a human being. The respiratory tract comprises an upper respiratory tract 10. The upper respiratory tract 10 includes the laryngopharyngeal region 9 from which the LP signal originates. The laryngopharyngeal region 9 forms a lower part of the upper respiratory tract 10. The upper respiratory tract 10 includes the nasal cavity, the pharynx, and the larynx. The laryngopharyngeal region 9 includes the pharynx and the larynx but not the nasal cavity, which is located above the laryngopharyngeal region.

Furthermore, the respiratory tract comprises a lower respiratory tract 12. The lower respiratory tract 12 includes the trachea and the lungs. The diaphragm, the major dome-shaped muscle of respiration, is located below the lungs and separates the thoracic cavity containing the heart and the lungs from the abdominal cavity. The region of the diaphragm 18 may herein be referred to as the diaphragmatic region.

Also shown in FIG. 2 is the esophagus, running alongside parts of the respiratory tract, including the laryngeal region of the upper respiratory tract 10.

Figure 3A:
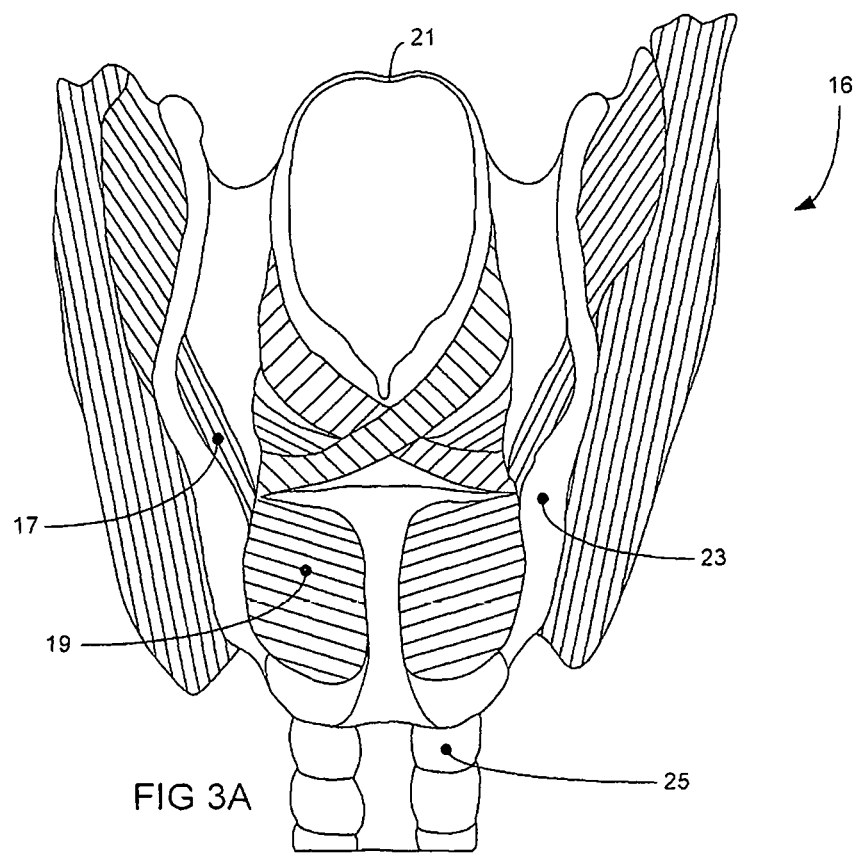
FIG. 3A is a posterior view of the larynx of a human being showing certain muscles in the laryngopharyngeal region.

FIG. 3A is a posterior view of the larynx 16 showing certain muscles in the laryngopharyngeal region 9. Of particular interest for the present invention is the glottal constrictor, namely the thyroarytenoid (TA) muscle 17, and the glottal dilator, namely the cricothyroid (CT) muscle 19. The epiglottis 21, the thyroid cartilage 23 and the first tracheal ring 25 are also indicated in the drawing for the purpose of orientation.

Figure 3B:
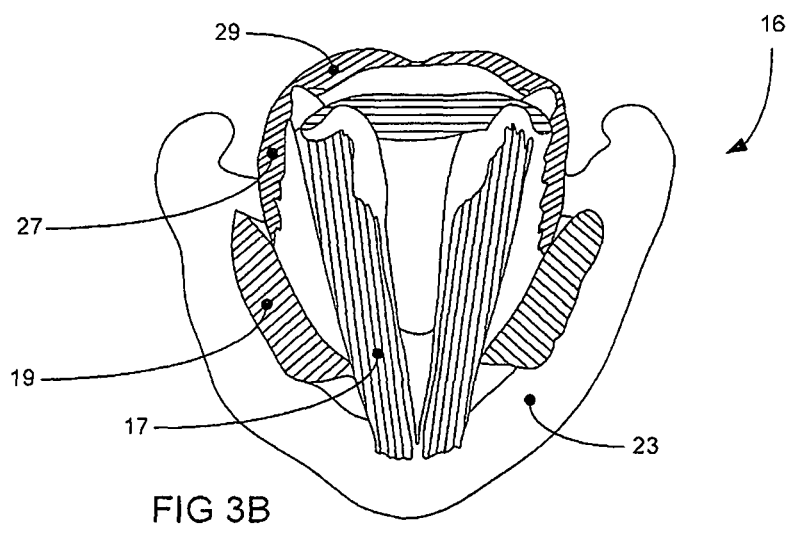
FIG. 3B is a top view showing some intrinsic muscles of the larynx of a human being, including the thyroarytenoid and cricothyroid muscles.

FIG. 3B is a top view showing some intrinsic muscles of the larynx 16, including said thyroarytenoid muscle 17 and said cricothyroid muscle 19. For the purpose of orientation, the thyroid cartilage 23, the lateral cricoarytenoid muscle 27 and the posterior cricoarytenoid muscle have also been indicated in the drawing.

Figure 4A:
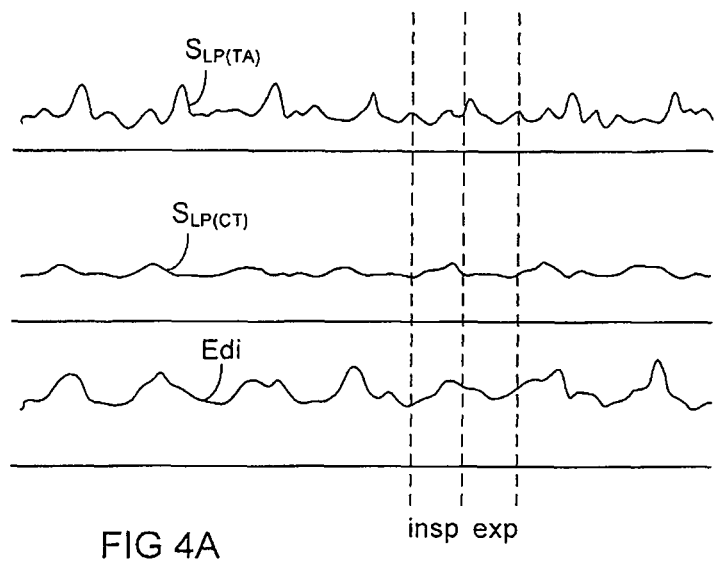
FIG. 4A illustrates the electrical activity of the thyroarytenoid muscle, the cricothyroid muscle, and the diaphragm of a patient undergoing NIV ventilation without continuous positive airway pressure.
Figure 4B:
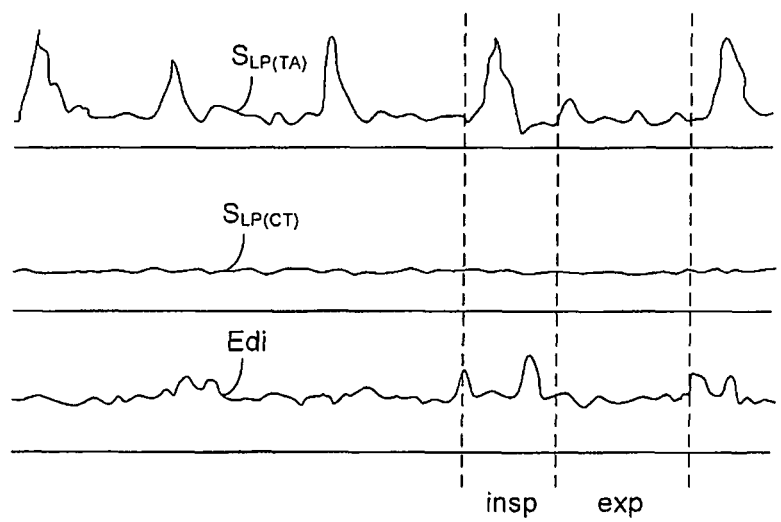
FIG. 4B illustrates the electrical activity of the thyroarytenoid muscle, the cricothyroid muscle, and the diaphragm of a patient undergoing NIV ventilation with pressure support.

FIGS. 4A and 4B each show three graphs illustrating the electrical activities of different muscles during NIV ventilation. FIG. 4A illustrates electrical muscle activity during NIV without continuous positive airway pressure (CPAP), and FIG. 4B illustrates electrical muscle activity during NIV with pressure support ventilation.

In each of FIGS. 4A and 4B, the upper graph illustrates a signal curve, SLP(TA), representing the electrical activity of the thyroarytenoid muscle 17, the middle graph illustrates a signal curve, SLP(CT), representing the electrical activity of the cricothyroid muscle 19, and the lower graph illustrates a signal curve, Edi, representing the electrical activity of the diaphragm. The vertical dashed lines indicate a ventilator inspiration phase (insp) and a ventilator expiration phase (exp) of the NIV ventilation. The signals SLP(TA) and SLP(CT) relating to the muscular activity of the TA and CT muscles, respectively, are examples of what is herein referred to as LP signals.

During spontaneous breathing, both the thyroarytenoid muscle 17 and cricothyroid muscles 19 are active—thyroarytenoid muscle activity occurring primarily at the end of inspiration. However, with application of pressure support ventilation, in particular during NIV, inspiratory cricothyroid activity disappears whereas activity of the thyroarytenoid muscle increases. This results in glottal narrowing and restricted ventilation, as seen in FIG. 4A.

In contrast to pressure support, glottal constrictor muscle activity (i.e. TA activity) does not increase with NAVA since NAVA induces less glottal closure and more synchronous ventilation. A possible underlying mechanism for the absence of glottal constrictor activity during inspiration with NAVA is that the pressure rise mimics the normal progressive recruitment of the diaphragmatic motor units, whereas during PSV, insufflation from the ventilator is performed with a constant level of pressure (decelerating flow pattern), often with a short inspiratory rise time to further decrease the patient's inspiratory work.

With reference now made to all previous drawings, the at least one LP signal, SLP, registered by the sensor arrangement 7 and used in accordance with the principles of the present invention, is related to muscular activity of at least one muscle in the laryngopharyngeal region 9 of the patient 3. Preferably, said at least one LP signal relates to the muscular activity of at least one laryngeal muscle, and even more preferably to the muscular activity of the TA muscle 17 and/or the CT muscle 19. Thus, the signals denoted SLP(TA) and SLP(CT) in FIGS. 4A and 4B, originating from the muscle activities of the TA and CT muscles, respectively, may, in some embodiments, constitute said LP signal.

The sensor arrangement 7 for measuring the at least one LP signal may comprise an optical sensor, such as a fiberoptic bronchoscope, for registering information indicative of the patency of the glottic aperture, and processing means configured to process the information registered by the optical sensor and generate an LP signal indicative of said patency and thus of the muscular activity of the laryngeal muscles and in particular the muscular activity of the TA and CT muscles. For example, said processing means may be configured to generate an LP signal the amplitude of which is proportional to the patency of the glottic opening. In some embodiments the optic sensor may be configured to capture images of the glottic opening, whereby said processing means may comprise image processing means for determining the patency, or degree of opening, of the glottic opening based on the captured images.

In a preferred embodiment, however, the sensor arrangement 7 for registering the at least one LP signal may be a bioelectric sensor arrangement configured to register LP signals in form of bioelectric signals originating from muscles in the laryngopharyngeal region 9.

Figure 5:
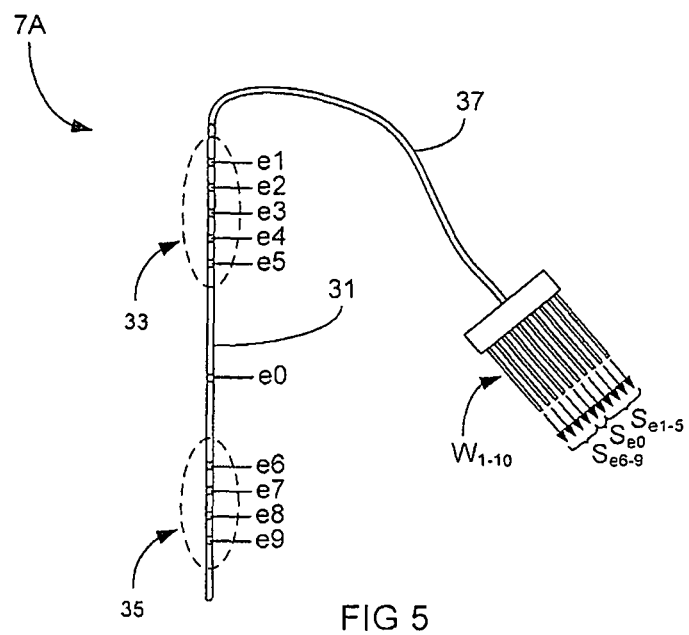
FIG. 5 illustrates a bioelectric sensor arrangement according to an exemplary embodiment of the invention.

FIG. 5 illustrates an exemplary embodiment of such a bioelectric sensor arrangement 7A. The bioelectric sensor arrangement 7A comprises an esophageal catheter 31 configured to be inserted into the esophagus of the patient 3. The esophageal catheter 31 comprises a plurality of electrodes e1-e5, herein referred to as laryngopharyngeal (LP) electrodes, located in an upper zone 33 in an upper part of the catheter 31. The LP electrodes e1-e5 are configured to register LP signals in form of EMG signals related to the muscular activity of at least one muscle in the laryngopharyngeal region 9, such as the TA and/or the CT muscle of the larynx 16. Such EMG signals related to laryngopharyngeal muscle activity are herein referred to as EMGLP signals.

The esophageal catheter 31 further comprises a plurality of diaphragm electrodes e6-e9, located in a lower zone 35 in a lower part of the catheter 31. The diaphragm electrodes e6-e9 are configured to register bioelectric signals in form of EMG signals related to the muscular activity of the diaphragm, which EMG signals are herein referred to as EMGDia signals.

The esophageal catheter 31 further comprises a reference electrode, e0, positioned in between said upper zone of LP electrodes and said lower zone of diaphragm electrodes.

Potential signals Se0-9, indicative of the potentials of the electrodes e0-e9 are transmitted from the electrodes e0-e9 towards a signal processing module (not shown) along electrode wires which are bundled together to form a single signal cable 37 proximate the catheter 31. In a more distal end, the electrode wires W1-10 are separated to allow connection of each electrode wire to a respective input of said signal processing unit.

The potential signals Se1-9 are indicative of the potentials of the electrodes e1-e9 in relation to the reference electrode e0. These signals Se1-9 are bioelectric raw signals comprising EMG components related to the activity of the laryngopharyngeal muscles and the diaphragmatic muscles. The bioelectric raw signals denoted Se1-5 registered by the LP electrodes e1-e5 comprises EMGLP components and constitute examples of what is herein referred to as the at least one LP signal. The bioelectric raw signals denoted Se6-9 registered by the diaphragm electrodes e6-e9 comprises EMGDia components and correspond to the bioelectric raw signals picked up by the electrodes of a conventional NAVA catheter.

The esophageal catheter 31 thus constitutes a novel type of NAVA catheter comprising two different groups of electrodes, e1-e5 and e6-e9, for registering EMGLP and EMGDia signals, respectively, in order to allow the operation of a ventilator to be controlled based on the muscular activity in both the laryngopharyngeal region 9 and the diaphragmatic region 18. This novel type of NAVA catheter is herein referred to as NAVADia/LP catheter.

Figure 6:
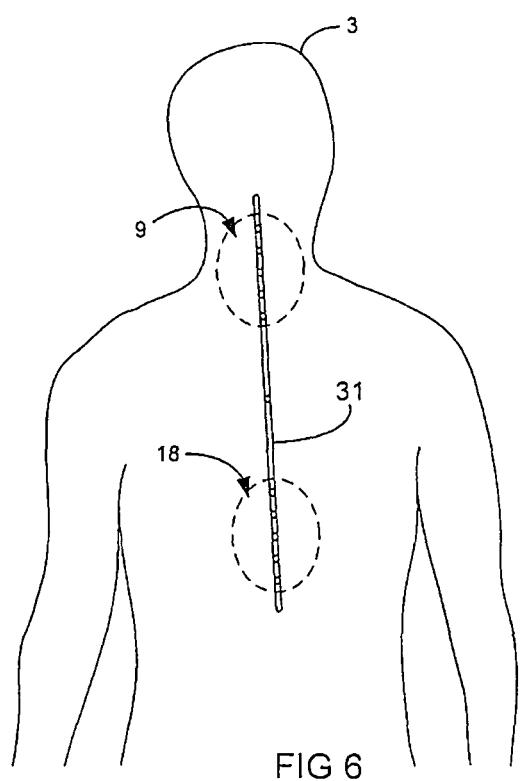
FIG. 6 illustrates the bioelectric sensor arrangement of FIG. 5 when inserted into the esophagus of a patient.

The upper zone 33 in which the LP electrodes e1-e5 are located is arranged on an upper half of the catheter 31, and the lower zone 35 in which the diaphragm electrodes e6-e9 are located is arranged on a lower half of the catheter 31. With reference now also made to FIG. 6, the catheter 31 and its upper 33 and lower 35 zones are dimensioned such that at least one LP electrode e1-e5, and preferably at least one LP electrode pair constituted by two adjacent LP electrodes, is positioned in the laryngopharyngeal region 9, at or near the larynx 16 of the patient 3, whereas at least one diaphragm electrode e6-e9, and preferably at least one diaphragm electrode pair constituted by two adjacent diaphragm electrodes, is positioned in the diaphragmatic region 18, at or near the diaphragm of the patient 3, when the esophageal catheter 31 is inserted into the esophagus of the patient.

The LP electrodes of the upper zone 33 are distributed along the length of said upper zone in the longitudinal direction of the catheter 31. Likewise, the diaphragm electrodes of the lower zone 35 are distributed along the length of the lower zone in the longitudinal direction of the catheter 31.

Preferably, the upper 33 and lower 35 zones of the catheter is separated by a distance of at least 5 cm, meaning that the vertical distance along the catheter, between the bottom LP electrode e5 and the top diaphragm electrode e6 is at least 5 cm. The length of the catheter 31 and the lengths of the upper 33 and lower zones 35 may be tailored to the anatomy of the patient 3.

Figure 7:
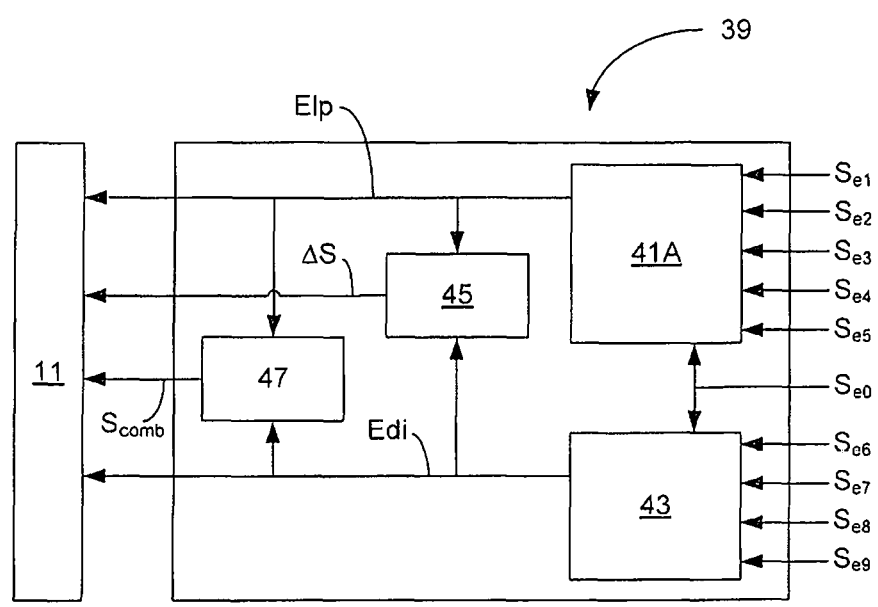
FIG. 7 illustrates a signal processing unit according to an exemplary embodiment of the invention, adapted for use with the bioelectric sensor arrangement of FIGS. 5 and 6.

FIG. 7 illustrates an exemplary embodiment of a signal processing unit 39 adapted for use with the NAVADia/LP catheter 31 in FIG. 5. The signal processing unit 39 is configured to receive and process the raw signals Se1-5 registered by the sensor arrangement 7A, and to transmit one or more signals derived from said raw signals Se1-5 to the at least one control unit 11 of the system, e.g. to be used as control signals in the control of the ventilator 5 (see FIG. 1).

The signal processing unit 39 comprises a module 41A, herein referred to as an EMGLP module, for receiving and processing the bioelectric raw signals Se1-5 registered by the LP electrodes e1-e5. The EMGLP module 41A is configured to process the raw signals Se1-5 in various ways, e.g. by reducing noise, in order to extract the EMGLP components. The extracted EMGLP signals are then further processed by the EMGLP module 41A to derive a signal reflecting the electrical activity of the at least one muscle of the laryngopharyngeal region, such as the TA muscle 17 or the CT muscle 19. This signal is herein referred to as the Elp signal, which signal can be said to correspond to the Edi signal of conventional NAVA (NAVADia).

The signal processing unit 39 further comprises a module 43, herein referred to as an EMGDia module, for receiving and processing the bioelectric raw signals Se6-9 registered by the diaphragm electrodes e6-e9. The EMGDia module 43 is configured to process the raw signals Se6-9 in various ways, e.g. by reducing noise and filtering out ECG components also comprised in the raw signals, in order to extract the EMGDia components from the raw signals. The extracted EMGDia signals are then further processed by the EMGDia module 43 to derive a signal reflecting the electrical activity of the diaphragm. This signal is the Edi signal commonly used to control the operation of ventilators operation in conventional NAVA mode (NAVADia).

As illustrated in the drawing, the EMGLP module 41A and the EMGDia module 43 further comprise a respective input for receiving the potential signal Se0 from the reference electrode e0. This signal may be used as reference signal by each of said modules 41A, 43 in the determination of the EMGLP and the EMGDia components, respectively, in a manner well-known in the art of electromyography.

The signal processing module 39 may further comprise a module, herein referred to as the comparator 45, configured to compare the Elp signal with the Edi signal. The at least one control unit of the system 11 may be configured to control the operation of the ventilation and/or to cause display of information on said at least one display unit 13A, 13B based on the result of said comparison. In this exemplary embodiment, the comparator 45 is configured to generate, based on said comparison, a reliability signal □S indicative of the reliability of any or both of said Elp and Edi signals. The comparator may for example be configured to generate said reliability signal based on the amplitudes of the Elp and Edi signals. It may also be configured to generate said reliability signal based on the synchrony/asynchrony of the Elp and Edi signals. The control unit 11 may be configured to generate an alarm if said reliability signal □S indicates that any or both of said Elp and Edi signals are currently unreliable. The alarm may be a visual and/or an audible alarm, e.g. a visual alarm displayed on a display unit 13A of the ventilator or the display unit 13B of the monitoring system 15. For example, if the reliability signal □S indicates asynchrony between the Elp signal and the Edi signal, which in turn indicates asynchrony between the muscular activities of the laryngopharyngeal muscles and the muscular activity of the diaphragm or faulty detection or processing of the signals from which the Elp and Edi signals are derived, an alarm signal may be generated notifying the ventilator operator that one or both of the Elp and Edi signals are probably unsuitable for use as a control signal for controlling the operation of the ventilator. As discussed above, asynchrony between the Elp signal and the Edi signal may also be due to the fact that the level of ventilatory assist provided by the ventilator is not optimal, or that the current PEEP level is not optimal.

In embodiments in which the operation of the ventilator 5 is controlled based on the Edi signal, said comparator 45 may be configured to compare the Edi signal with the Elp signal to validate the reliability of the Edi signal. The control unit 11 may be configured to cause interruption of the Edi-controlled NAVA ventilation in case the comparison indicates that the Edi signal is unreliable. For example, in case the comparison shows that the Edi signal is unreliable, the control unit 11 may be configured to cause the ventilator 5 to switch from the current Edi-controlled mode of operation to a ventilation mode not dependent on said Edi signal, e.g. to a pneumatic support mode, such as a pressure support or volume support mode.

The signal processing module 39 may further comprise a module, hereinafter referred to as the combiner 47, configured to combine the Elp signal and the Edi signal into a combined signal Scomb based on both said Elp signal and said Edi signal. This combined signal Scomb may be used in addition or instead of the Elp and/or the Edi signal as a control signal for controlling the operation of the ventilator.

The signals Elp, □S and Scomb are all examples of signals derived from LP signals related to laryngopharyngeal muscle activity, which signals may be used in accordance with the principles of the present invention to provide improved neural control of a ventilator 5 providing support ventilation to a patient 3.

Figure 8:
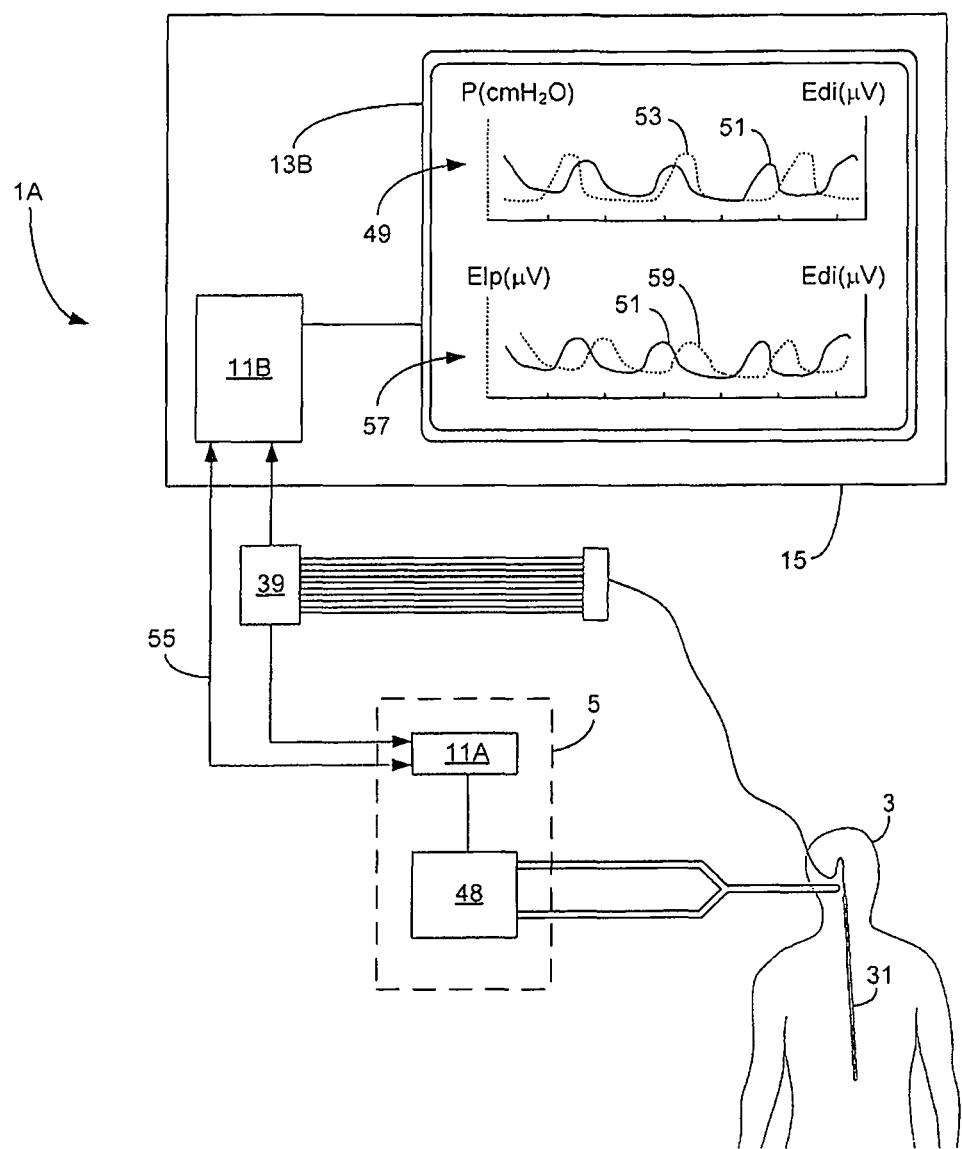
FIG. 8 illustrates a system for use in connection with mechanical ventilation of a patient, according to another exemplary embodiment of the invention.

FIG. 8 illustrates another exemplary embodiment of a system 1A according to the present disclosure. The system 1A is seen to comprise a sensor arrangement 7A as described above with reference to FIG. 5, a signal processing unit 39 as described above with reference to FIG. 7, a ventilator 5 providing support ventilation to a patient 3, and a monitoring system 15 for monitoring patient and ventilator parameters. The signal processing unit 39 is coupled to an internal control unit 11A of the ventilator 5, configured to control the operation of the ventilator based on the Edi signal derived from the EMGDia signals, i.e. to operate the ventilator in a conventional NAVA mode. To this end, the control unit 11A is configured to transmit control signals to a gas regulating unit 48 of the ventilator 5 in dependence of the Edi signal.

The signal processing unit 39 is also coupled to an internal control unit 11B of the monitoring system 15, configured to cause display of signals and/or information contained in the signals received from the signal processing unit 39, and derived from the bioelectric signals Se1-9 captured by the sensor arrangement 7A. The display unit 13B of the monitoring system is seen to comprise a first display window 49 showing a first signal curve 51 representing the Edi signal, and a second signal curve 53 representing a the proximal patient pressure, i.e. a pressure substantially corresponding to the airway pressure of the patient 3, which pressure may be measured by means of a pressure sensor of the ventilator 5 and communicated to the monitoring system 15 via a communication connection 55. The display unit 13B further comprises a second display window 57 showing said Edi signal curve 51 together with a second signal curve 59 representing the Elp signal derived from the signals Se1-5 and related to the laryngopharyngeal muscle activity of the patient 3. The Edi signal curve 51 and the Elp signal curve 59 are associatively displayed in a common display window 57 in order for an operator of the ventilator 5 to easily compare the Edi signal and the Elp signal. The monitoring system 15 is hence configured to associatively display information related to the muscular activity of the diaphragm of the patient 3 and information related to the muscular activity of at least one muscle in the laryngopharyngeal region of the patient 3. The information is preferably displayed in a common frame of reference in order to facilitate comparison between the information contents, e.g. by displaying the Edi and Elp signal curves in a common time frame.

Although illustrated as a separate external unit in this exemplary embodiment, it should be appreciated that the signal processing unit 39 may also be integrated into the ventilator 5 or the monitoring system 15. In this case, information derived by the signal processing unit 39 could still be supplied to both the ventilator 5 and the monitoring system 15, e.g. by transmitting the information via the communication connection 55. In some embodiments, the signal processing unit 39 may be integrated in the ventilator 5 to form a module intended to replace the Edi module of conventional NAVA-enabled ventilators, so as to adapt the ventilator 5 for the enhanced NAVADia/LP functionality described herein.

Figure 9:
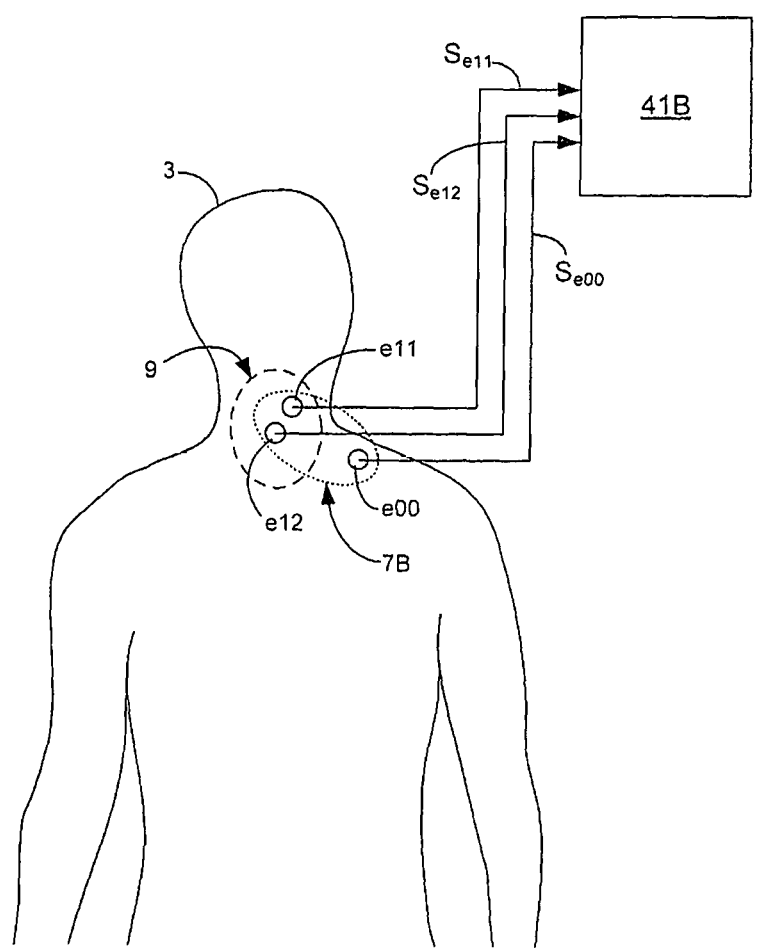
FIG. 9 illustrates a bioelectric sensor arrangement according to another exemplary embodiment of the invention.

FIG. 9 illustrates a bioelectric sensor arrangement 7B according to another embodiment of the present disclosure.

This bioelectric sensor arrangement 7B comprises a set of surface electrodes for registering the at least one LP signal non-invasively from outside the patient 3. In this exemplary embodiment, the bioelectric sensor arrangement 7B comprises two surface electrodes e11 and e12 which are attached to the skin of the patient's neck, outside the laryngopharyngeal region 9 of the upper airways of the patient 3. Just like the LP electrodes e1-e5 of the esophageal catheter 31 described above with reference to FIG. 5, the surface electrodes e11, e12 of the bioelectric sensor arrangement 7B are configured to register potential signals Se11, Se12 in form of bioelectric raw signals carrying information of the EMGLP of the patient 3, which signals hence constitute another example of what is herein referred to as LP signals. For the sake of consistency in terminology, the electrodes e11 and e12 serving to register said LP signals are hereinafter referred to as LP electrodes of the bioelectric sensor arrangement 7B. The bioelectric raw signals Se11, Se12 registered by the LP electrodes e11, e12 are transmitted to an EMGLP module 41B similar to the EMGLP module 41A in FIG. 7.

Consequently, the EMGLP module 41B is configured to process the raw signals Se11, Se12 in various ways, e.g. by reducing noise, in order to extract the EMGLP components of said raw signals. The extracted EMGLP signals may then be further processed by the EMGLP module 41B to derive the above mentioned Elp signal reflecting the electrical activity of the at least one muscle of the laryngopharyngeal region, such as the TA muscle 17 or the CT muscle 19 (see FIGS. 3A and 3B).

The bioelectric sensor arrangement 7B is further seen to comprise a reference electrode e00. The potential signal Se00 registered by the reference electrode e00 may also be transmitted to the EMGLP module 41B in order to be used by said module as reference signal in the determination of the EMGLP components of the raw signals Se11, Se12, in a manner well-known in the art of electromyography.

With simultaneous reference to previous drawings, and in particular FIGS. 1 and 8, it should be appreciated that the EMGLP module 41B, although not illustrated in FIG. 9, is coupled to the at least one control unit 11, 11A, 11B of the system 1, 1A of the present disclosure in order for said at least one control unit to control the operation of the ventilator 5 based on the LP signals Se11, Se12 registered by the bioelectric sensor arrangement 7B, and typically based on an Elp signal derived from said LP signals, and/or to cause display of information related to said LP signals on at least one display unit 13A, 13B for monitoring the patient 3 and/or the operation of the ventilator 5, e.g. display of a signal curve representing said Elp signal.

Furthermore, it should be appreciated that the bioelectric sensor arrangement 7B for surface detection of LP signals may be advantageously used in combination with at least one other bioelectric sensor arrangement for detection of bioelectric signals representative of the EMGDia of the patient 3, such as a conventional NAVA catheter and/or another set of surface electrodes positioned outside the diaphragmatic region of the patient 3 and configured to register such bioelectric signals from the surface of the patient's skin. In this case, the at least one control unit 11, 11A, 11B of the system 1, 1A may be configured to control the operation of the ventilator 5 and/or to cause display information on said at least one display unit 13A, 13B based on both the LP signals representative of the EMGLP of the patient 3, captured by the surface electrodes e11 and e12, and the bioelectric signals representative of the EMGDia of the patient 3, in accordance with any of the principles described above.

In this case, the EMGLP module 41B may form part of a signal processing unit (not shown) configured to derive an Elp signal from the signals registered by the LP surface electrodes e11, e12 of the bioelectric sensor arrangement 7B, which signal processing unit is further configured to derive an Edi signal from bioelectric signals representative of the EMGDia of the patient 3, captured by and received from said at least one other sensor arrangement. Thus, it should be appreciated that the EMGLP module 41B may form part of a signal processing unit similar to the signal processing unit 39 of FIG. 7, in which the EMGLP module 41A for determination of an Elp signal based on the LP signals captured by the LP electrodes e1-e5 of the esophageal catheter 31 is replaced by the EMGLP module 41B for determination of an Elp signal based on the LP signals captured by the LP surface electrodes e11, e12, and in which the EMGDia module 43 may or may not be replaced by another EMGDia module for determination of an Edi signal based on bioelectric signals representative of the EMGDia of the patient 3, captured by said at least one other sensor arrangement.

As previously discussed, the registered LP signals may be used to improve mechanical ventilation in many different ways in different modes of ventilation. In the following, some exemplary methods of use of the at least one registered LP signal will be described with reference to various flow charts. Unless stated otherwise, the methods are carried out by the at least one control unit 11 of the system 1 by executing a computer program stored in a memory of said control unit 11 by means of a processing unit, such as a microprocessor.

Figure 10:
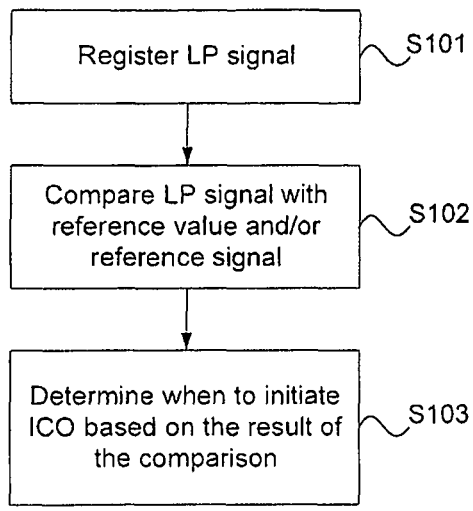
FIG. 10 is a flowchart illustrating a method for determining when during ventilator inspiration to initiate inspiratory cycle-off (ICO), according to an exemplary embodiment of the invention.

FIG. 10 is a flow chart illustrating a method for determining, based on the at least one registered LP signal, when, during ventilator inspiration, to initiate inspiratory cycle-off (ICO), i.e. when to cause the ventilator to switch from an inspiratory phase to an expiratory phase.

In a first step, S101, at least one LP signal related to muscular activity of at least one muscle in the laryngopharyngeal region of a patient undergoing ventilatory treatment is registered.

In a second step, S102, the at least one registered LP signal is compared with a reference value and/or a reference signal. Said reference value may be a threshold value serving as an LP signal trigger level for initiation of ICO, and said reference signal may be a currently available Edi signal of the patient.

In a third step, S103, a point in time at which to initiate ICO, i.e. a point in time at which to switch from ventilator inspiration to ventilator expiration, is determined based on the result(s) of the comparison(s) in step S102.

Figure 11:
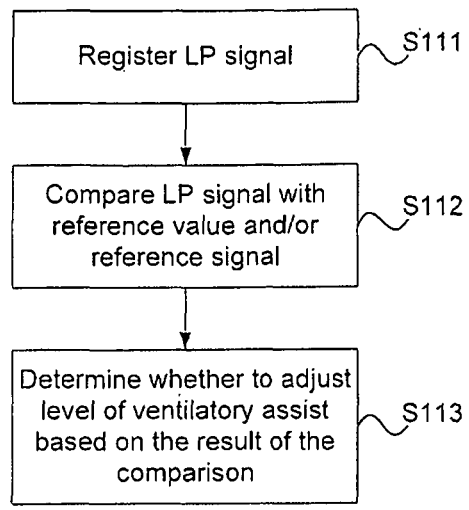
FIG. 11 is a flowchart illustrating a method for determining if a level of ventilatory assist currently provided to a patient by a ventilator should be adjusted, according to an exemplary embodiment of the invention.

FIG. 11 is a flow chart illustrating a method for determining, based on the at least one registered LP signal, if a level of ventilatory assist currently provided to a patient by a ventilator should be adjusted.

In a first step, S111, at least one LP signal related to muscular activity of at least one muscle in the laryngopharyngeal region of the patient is registered.

In a second step, S112, the at least one registered LP signal is compared with a reference value and/or a reference signal. Said reference value may be a threshold value indicating too high level of ventilatory assist, and said reference signal may be a currently available Edi signal of the patient. Preferably, the comparison is made using an inspiratory LP signal, i.e. an LP signal registered during ventilator inspiration.

In a third step, S113, it is determined whether the level of ventilatory assist should be adjusted based on the result(s) of the comparison(s) in step S112.

If it is determined that the level of ventilatory assist should be adjusted, i.e. that the level of ventilatory assist currently provided to the patient is too high or too low, the method may comprise a subsequent step (not shown) in which the level of ventilatory assist is automatically adjusted, and/or in which a signal indicating that the level of ventilatory assist should be adjusted is generated so as to notify an operator of the ventilator thereof.

Figure 12:
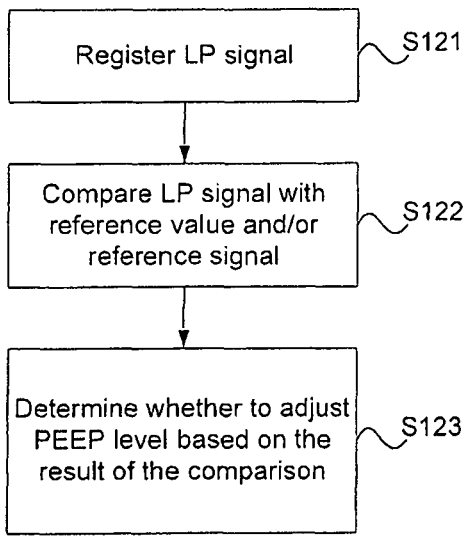
FIG. 12 is a flowchart illustrating a method for determining if a level of PEEP currently applied to a patient by a ventilator should be adjusted, according to an exemplary embodiment of the invention.

FIG. 12 is a flow chart illustrating a method for determining, based on the at least one registered LP signal, if a level of PEEP currently applied to a patient by a ventilator should be adjusted.

In a first step, S121, at least one LP signal related to muscular activity of at least one muscle in the laryngopharyngeal region of the patient is registered.

In a second step, S122, the at least one registered LP signal is compared with a reference value and/or a reference signal. Said reference value may be a threshold value indicating too low PEEP level, and said reference signal may be a currently available Edi signal of the patient. Preferably, the comparison is made using an expiratory LP signal, i.e. an LP signal registered during ventilator expiration.

In a third step, S123, it is determined whether the PEEP level should be adjusted based on the result(s) of the comparison(s) in step S122.

If it is determined that the PEEP level should be adjusted, i.e. that the PEEP currently applied to the patient is too high or too low, the method may comprise a subsequent step (not shown) in which the PEEP level is automatically adjusted, and/or in which a signal indicating that the PEEP level should be adjusted is generated so as to notify an operator of the ventilator thereof.

Figure 13:
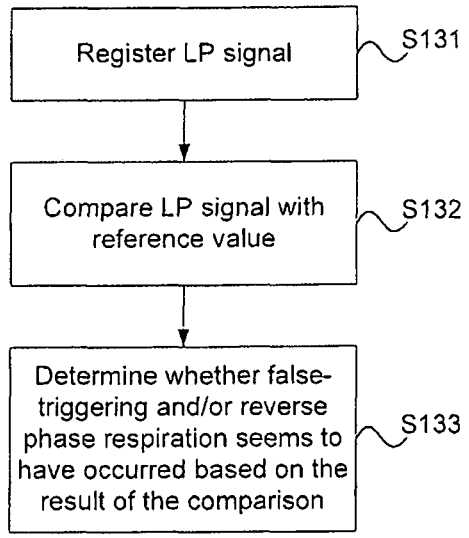
FIG. 13 is a flowchart illustrating a method for detecting false triggering of respiration phases in patient-triggered ventilation modes, and/or reverse phase respiration, according to an exemplary embodiment of the invention.

FIG. 13 is a flow chart illustrating a method for detecting, based on the at least one registered LP signal, false triggering of respiration phases, in particular inspiration phases, in patient-triggered ventilation modes, and/or reverse phase respiration, i.e. a situation in which the respiratory phases of the ventilator and the patient are reversed in relation to each other.

In a first step, S131, at least one LP signal related to muscular activity of at least one muscle in the laryngopharyngeal region of the patient is registered.

In a second step, S132, the at least one registered LP signal is compared with a reference value. For example, the comparison may be made between the inspiratory LP signal, i.e. a part of the LP signal registered during ventilator inspiration, and a threshold value for said inspiratory LP signal. If the inspiratory LP signal exceeds said threshold value it is an indication of false-triggering of the ventilator inspiration phase and/or an indication of reverse phase respiration of the ventilator and the patient, given that the level of ventilatory assist currently provided to the patient is not too high.

In a third step, S133, it is determined, based on the result of the comparison in step S132, whether false-triggering and/or reverse phase respiration seems to have occurred.

If it is determined in step 133 that false-triggering and/or reverse phase respiration is likely to have occurred, the method may comprise a subsequent step (not shown) in which the operation of the ventilator is automatically adjusted to avoid or at least mitigate the risk of false-triggering and/or reverse phase respiration, and/or in which a signal indicating the detection of false-triggering and/or reverse phase respiration is generated in order to notify an operator of the ventilator thereof.

Definitions and Abbreviations

EMG Electromyogram
EMGLP EMG representative of laryngopharyngeal muscle activity
EMGDia EMG representative of diaphragmatic muscle activity
LP Laryngopharynx/laryngopharyngeal
NAVA Neurally adjusted ventilatory assist
NAVADia Diaphragmatic NAVA; Conventional NAVA wherein ventilation is controlled based on signals related to the muscular activity of the diaphragm
NAVALP Laryngopharyngeal NAVA; Novel type of NAVA wherein ventilation is controlled based on signals related to the muscular activity of muscles in the laryngopharyngeal region
NAVADia/LP Diaphragmatic/Laryngopharyngeal NAVA; Novel type of NAVA wherein ventilation is controlled based on both signals related to the muscular activity of the diaphragm and signals related to the muscular activity of muscles in the laryngopharyngeal region
NAVA (PS) Pressure support mode of NAVA-enabled ventilator
PSV Pressure support mode
VSV Volume support mode Although modifications and changes may be suggested by those skilled in the art, it is the intention of the Applicant to embody within the patent warranted hereon all changes and modifications as reasonably and properly come within the scope of the Applicant's contribution to the art.

The invention claimed is:

1. A system for use in connection with mechanical ventilation of a patient, provided by a ventilator, said system comprising:
    a bioelectric sensor arrangement configured to register at least one bioelectric signal (LP signal) originating from and relating to muscular activity of at least one muscle in the laryngopharyngeal region of said patient, and
    at least one controller configured to control operation of said ventilator based on said at least one LP signal,
    wherein the at least one controller is configured to use said at least one LP signal together with at least one other signal related to the muscular activity of the patient's diaphragm, in the control of the operation of said ventilator.

2. System according to claim 1, wherein said at least one controller is configured to use said at least one LP signal to control the operation of said ventilator when operated in a support ventilation mode being either a pneumatic support mode or a NAVA mode.

3. System according to claim 1, wherein said at least one other signal related to the muscular activity of the patient's diaphragm is used as a control signal to control the operation of the ventilator, the at least one controller being configured to use the at least one LP signal to validate the reliability of said at least one other signal.

4. System according to claim 1, wherein said sensor arrangement comprises an oesophageal catheter comprising at least one electrode (LP electrode), configured to register said at least one LP signal in the laryngopharyngeal region of the patient.

5. System according to claim 4, wherein said oesophageal catheter comprises at least one further electrode (diaphragm electrode), configured to register the at least one other signal related to the muscular activity of the patient's diaphragm.

6. System according to claim 5, wherein the oesophageal catheter has a length along which the at least one LP electrode and the at least one diaphragm electrode are positioned, the catheter being configured such that said length and said positions causes said at least one LP electrode to be positioned in the laryngopharyngeal region of the patient and the at least one diaphragm electrode to be positioned in a diaphragmatic region of the patient, when the oesophageal catheter is inserted as intended into the oesophagus of the patient.

7. System according to claim 5, further comprising a signal processor configured to receive said at least one LP signal and said at least one other signal, and to process said signals differently in order to derive, from the at least one LP signal, a first processed signal indicative of the electrical activity of at least one muscle in the laryngopharyngeal region, and to derive, from the at least one other signal, a second processed signal indicative of the electrical activity of the diaphragm.

8. System according to claim 1, wherein said at least one controller is configured to use said at least one LP signal to determine when to switch from one respiratory phase of the ventilator to another.

9. System according to claim 8, wherein said at least one controller is configured to determine when to initiate an inspiratory cycle-off by determining when said at least one LP signal exceeds a certain threshold value serving as a trigger level for said inspiratory cycle-off.

10. System according to claim 1, wherein said at least one controller is configured to use said at least one LP signal to determine whether a current level of ventilatory assist provided to the patient by the ventilator should be adjusted.

11. System according to claim 10, wherein said at least one controller is configured to determine whether the level of ventilatory assist should be adjusted by determining if the LP signal registered during ventilator inspiration exceeds a certain threshold value.

12. System according to claim 1, wherein said at least one controller is configured to use said at least one LP signal to determine whether a current PEEP level applied to the patient by the ventilator should be adjusted.

13. System according to claim 12, wherein said at least one controller is configured to determine whether the PEEP level should be adjusted by determining if the LP signal registered during ventilator expiration exceeds a certain threshold value.

14. System according to claim 1, wherein said at least one controller is configured to use said at least one LP signal to detect ventilator-patient asynchrony.

15. System according to claim 1, wherein said at least one controller is configured to use said at least one LP signal to detect false-triggering of patient-triggered respiration phases and/or reverse phase respiration.

16. System according to claim 1, wherein the at least one registered LP signal is related to muscular activity of at least one laryngeal muscle of the patient.

17. System according to claim 1, wherein the at least one registered LP signal is related to muscular activity of the thyroarytenoid muscle and/or the cricothyroid muscle of the patient.

18. System according to claim 1, wherein the at least one controller is configured to cause display of information related to said at least one LP signal on a display unit for monitoring said patient and/or the operation of the ventilator.

19. A non-transitory, computer-readable data storage medium encoded with programming instructions, said storage medium being loaded into a control computer of a ventilator having a bioelectric sensor arrangement for registering at least one bioelectrical signal (LP signal) originating from and relating to muscular activity of at least one muscle in the laryngopharyngeal region of the patient, and said programming instructions causing said control computer to:
receive, from said bioelectric sensor arrangement, said at least one LP signal; and
control operation of said ventilator based on said at least one LP signal received from said bioelectric sensor arrangement,
wherein said programming instructions cause said control computer to use said at least one LP signal together with at least one other signal related to the muscular activity of the patient's diaphragm, in the control of the operation of said ventilator.

* * * * *